United States Patent [19]

Vacanti

[11] 4,102,748

[45] Jul. 25, 1978

[54] DEVICE FOR PLATING AND STREAKING A MICROBIOLOGICAL SAMPLE

[76] Inventor: Mary Frances Vacanti, Omaha, Nebr.

[21] Appl. No.: 850,040

[22] Filed: Nov. 9, 1977

[51] Int. Cl.² .......................... C12B 1/02; C12K 1/04
[52] U.S. Cl. ........................................ 195/127; 23/292
[58] Field of Search ................. 23/292; 195/120, 127;
73/425, 425.4 R, 425.4 P; 46/6, 7; 427/2;
118/100, 506; 15/104 S

[56] References Cited

U.S. PATENT DOCUMENTS

| 781,250 | 1/1905 | Welch | 15/236 R |
|---|---|---|---|
| 2,527,935 | 10/1950 | Joel | 46/6 |
| 3,077,780 | 2/1963 | Takatsy | 73/425.4 P |
| 3,144,950 | 8/1964 | Rosenheim | 46/7 X |
| 3,147,197 | 9/1964 | Conners | 23/292 X |
| 3,191,813 | 6/1965 | Duff | 73/425.4 P |
| 3,742,187 | 6/1973 | Folus | 195/120 X |
| 4,010,077 | 3/1977 | Pardos | 195/120 X |

FOREIGN PATENT DOCUMENTS 464,907  7/1975  U.S.S.R. ........................ 46/6

Primary Examiner—Morris Kaplan

[57] ABSTRACT

A three plane instrument for plating and streaking a microbiological sample has a hand held stem topped by a conventional first planar loop for forming a film by dipping and at least one partial planar loop co-extensive with the first loop and having one leg spaced from and parallel thereto. After plating, the stem is rotated and the said leg is utilized to streak the plated sample.

3 Claims, 1 Drawing Figure

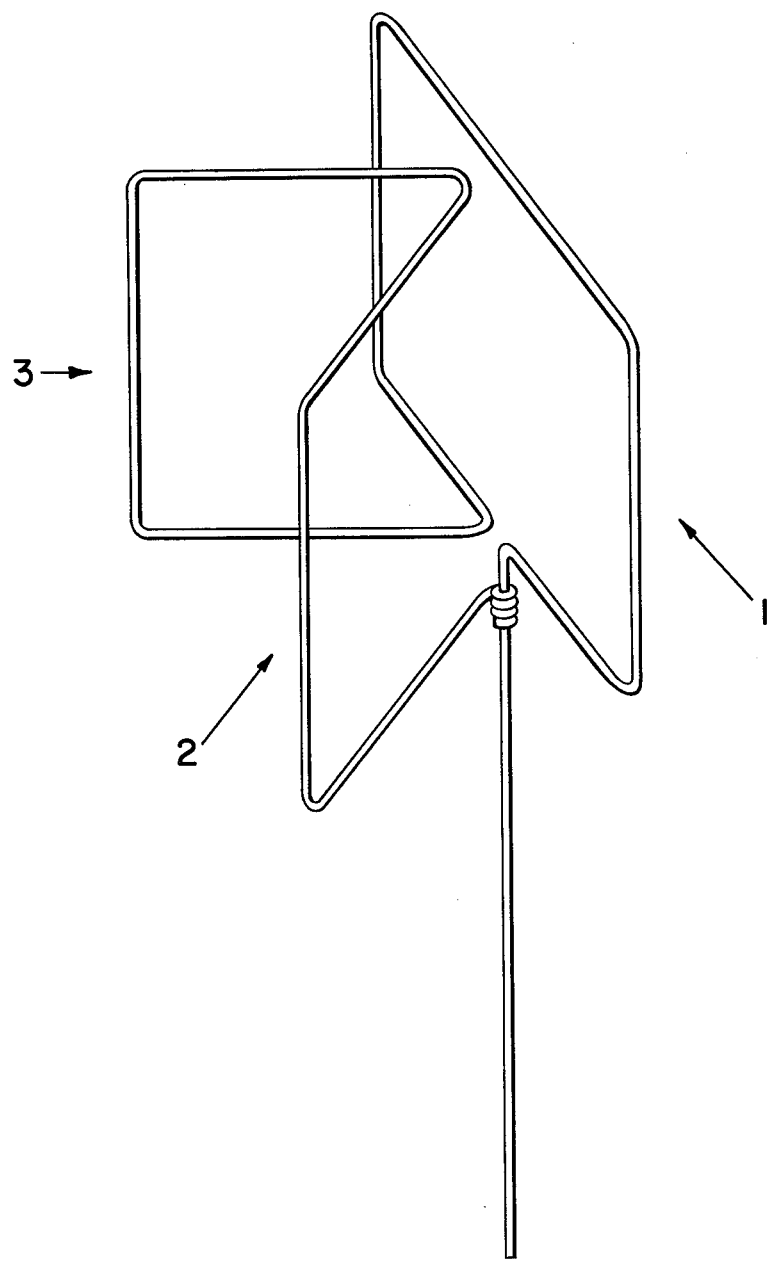

DEVICE FOR PLATING AND STREAKING A MICROBIOLOGICAL SAMPLE

The present invention relates to a device for plating and streaking a biological sample.

It is known to use a single loop instrument for plating and streaking but the practice has a disadvantage in that the single loop device requires intermittent burning when used for both plating and streaking.

An object of the present invention is to provide a device utilizable to avoid the requirement of burning during plating and streaking of a microbiological sample.

A further object of the invention is to provide a three-plane, hand held device formed of three planar loops wherein a first conventional loop is utilized for plating, the device rotated and a leg of at least one additional loop is utilized for streaking.

The sole FIGURE of drawing is a perspective view of the device.

The device in brief comprises relatively thin gauge material forming three planar loops mounted on or topping a stem element which is adapted to be hend held. The loops are generally coextensive in height, lie in planes about sixty degree from one another and two of the planar loops are preferrably smaller than and located on the same side of the third loop.

The length of an instrument, excluding the interchangeable handle, is 75 millimeters. The larger loop is 8 millimeters by 5 millimeters. The remaining loops measure 5 millimeters by 5 millimeters. Loop number three measures 5 millimeters by 5 millimeters. These measurements are one possibility and other measurements would work equally well. One piece of wire is bent into the configuration using soft angles. The two free ends can be twisted together giving the instrument greater stability. This instrument can be made by bending a single piece of wire into loops that exist in multiple planes. The instrument can be made of platinum, chromium, tungsten, nickel, or any other suitable metal that can be heated rapidly and cooled rapidly. The guage of the wire may vary from 20 to 29. The instrument can also be cast from a mold or welded. It can also be made from plastic, individually wrapped and sterilized for one-time use, and not require flaming if the initial inoculum is put on with a sterile swab or any other suitable instrument. The important feature of the instrument is that it consists of loops that exist in multiple planes, and the shape of the loops can be of squares, rectangles, circles, or a variety of geometric configurations. In using the instrument, the wire loop is first flamed. The sample is then picked up with the larger loop and is planted and streaked on the plate. The instrument is flamed and loop number one is used to pass through the streaked area, obtaining some planted material, and this material is then streaked onto a clean portion of the media. The plate is then rotated approximately seventy degrees and the instrument is also rotated bringing the edge of loop number two into functional position. The plate is again streaked with the edge of loop number two as is done in conventional plate streaking. The plate is again rotated and the instrument is again rotated bringing the edge of loop number three into functional position. The plate is again streaked in the manner as in conventional plate streaking.

I claim:

1. A manually manipulable device for plating and streaking a microbiological sample comprising:
   a stem element adapted to be hand held for manipulation thereof;
   a generally closed planar loop, formed of a relatively thin gauge material and topping said stem, whereby a specimen of said microbiological sample may be obtained by dipping and whereby said specimen may be plated onto a substrate;
   at least two partial planar loops, coextensive in height with the generally closed loop, and extending from one side of and without touching the plane of said generally closed loop, and at angles of about 60° from each other and said generally closed loop, and each partial loop having a generally vertical leg section of said coextensive height spaced from said closed loop; and
   said partial loops being fabricated of a relatively thin gauge material;
   whereby after said plating, the device may be rotated and said leg utilized to streak said specimen.

2. A device according to claim 1 wherein the device is fabricated of a single continuous length wire.

3. A device according to claim 1 wherein the device is a molded plastic.

* * * * *